(12) United States Patent
Lange et al.

(10) Patent No.: US 6,720,073 B2
(45) Date of Patent: Apr. 13, 2004

(54) MATERIAL ENHANCEMENT TO MAINTAIN HIGH ABSORBENT CAPACITY UNDER HIGH LOADS FOLLOWING RIGOROUS PROCESS CONDITIONS

(75) Inventors: Nancy Birbiglia Lange, Oshkosh, WI (US); William Grover Reeves, Appleton, WI (US); Shannon Kathleen Melius, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 3 days.

(21) Appl. No.: 10/036,755

(22) Filed: Dec. 21, 2001

(65) Prior Publication Data

US 2002/0150761 A1 Oct. 17, 2002

Related U.S. Application Data

(63) Continuation-in-part of application No. 09/545,156, filed on Apr. 7, 2000, now Pat. No. 6,387,495.

(51) Int. Cl.⁷ .................................................. B32B 5/66
(52) U.S. Cl. ...................... 428/403; 428/407; 428/327; 428/295.1; 428/297.4; 428/339; 523/201; 523/206; 523/105; 424/402; 424/484; 424/486; 424/487; 604/365; 604/368; 604/372; 604/374; 604/375; 604/367
(58) Field of Search .............................. 428/327, 295.1, 428/403, 407, 339, 297.4; 523/201, 206, 105; 524/918; 526/930; 424/402, 484, 486, 487; 604/365, 368, 372, 374, 375, 367

(56) References Cited

U.S. PATENT DOCUMENTS

| | | |
|---|---|---|
| 3,901,236 A | 8/1975 | Assarsson et al. |
| 5,102,597 A | 4/1992 | Roe et al. |
| 5,124,188 A | 6/1992 | Roe et al. |
| 5,147,343 A | 9/1992 | Kellenberger |
| 5,230,959 A | 7/1993 | Young, Sr. et al. |
| 5,368,918 A | 11/1994 | Harada et al. |
| 5,436,066 A | 7/1995 | Chen |
| 5,447,727 A | 9/1995 | Graham |
| 5,489,469 A | 2/1996 | Kobayashi et al. |
| 5,601,542 A | 2/1997 | Melius et al. |
| 5,713,881 A | 2/1998 | Rezai et al. |
| 5,800,418 A | 9/1998 | Ahr |
| 5,843,575 A | 12/1998 | Wang et al. |
| 5,849,405 A | 12/1998 | Wang et al. |
| 5,851,672 A | 12/1998 | Wang et al. |
| 5,855,571 A | 1/1999 | Steger et al. |
| 5,858,535 A | 1/1999 | Wang et al. |
| 5,859,074 A | 1/1999 | Rezai et al. |
| 5,868,724 A | 2/1999 | Dierckes, Jr. et al. |
| 5,998,032 A | 12/1999 | Hansen et al. |
| 6,103,785 A | 8/2000 | Kajikawa et al. |
| H1909 H | 11/2000 | Ahr |
| 6,214,274 B1 | 4/2001 | Melius et al. |
| 6,239,230 B1 | 5/2001 | Eckert et al. |
| 6,387,495 B1 * | 5/2002 | Reeves et al. ............... 428/402 |
| 6,414,214 B1 * | 7/2002 | Engelhardt .................. 604/368 |

FOREIGN PATENT DOCUMENTS

| | | |
|---|---|---|
| EP | 0 339 461 B1 | 1/1993 |
| EP | 1 029 886 | 8/2000 |
| WO | 96/14885 | 5/1996 |
| WO | 97/27884 | 8/1997 |
| WO | 98/48857 | 11/1997 |
| WO | 99/63923 | 12/1999 |
| WO | 00/69383 | 11/2000 |
| WO | 02/076520 | 10/2002 |
| WO | 02/077347 | 10/2002 |

\* cited by examiner

*Primary Examiner*—Leszek Kiliman
(74) *Attorney, Agent, or Firm*—Pauley Petersen & Erickson

(57) ABSTRACT

An absorbent composite that can handle complex fluids and maintain high absorbent capacity under high loads even after the material has been subjected to rigorous processing conditions. The absorbent composite includes an inhomogeneously crosslinked superabsorbent polymer having a highly crosslinked outer shell. The surface of the superabsorbent polymer includes a protective fibrous coating material and an association agent.

91 Claims, 3 Drawing Sheets

MATERIAL ENHANCEMENT TO MAINTAIN HIGH ABSORBENT CAPACITY UNDER HIGH LOADS FOLLOWING RIGOROUS PROCESS CONDITIONS

CROSS REFERENCE TO RELATED APPLICATION

This application is a continuation-in-part application of U.S. patent application Ser. No. 09/545,156 filed Apr. 7, 2000 now U.S. Pat. No. 6,387,495.

BACKGROUND OF THE INVENTION

The present invention relates to an absorbent composite capable of handling simple and complex fluids and maintaining high absorbent capacity under high loads even after the material has been subjected to rigorous processing conditions.

Superabsorbent materials possess a number of attributes that make them attractive in many different applications. As a result of their superior water-absorbing attributes, superabsorbent materials have supplanted much of the traditional absorbents in disposable diapers and have made significant improvements in the performance of disposable feminine hygiene products and disposable adult incontinence products. The basic property of water absorption has suggested the use of superabsorbent materials in many other applications, including paper towels, surgical sponges, meat trays, disposable mats for outside doorways and in bathrooms, and for household pet litter, bandages and wound dressings.

The largest use of superabsorbent materials, however, is in disposable personal hygiene products. These products include, in order of volume of superabsorbent material used, diapers, training pants, adult incontinence products and feminine hygiene products. Of these, diapers accounted for over 90% of the total superabsorbent material sold in 1995. Because of this, the development of superabsorbent properties in general has been focused on optimizing absorbency of urine.

A challenge for the developers of products into which superabsorbent materials are incorporated, however, is the very significant difference between the fluids to be absorbed by the various disposable absorbent products. With diapers, for example, the fluid is typically urine, a simple fluid of primarily water, salts and nitrogenous materials such as urea. With feminine hygiene products, for example, the fluid is typically menses, a complex fluid including water, salts, and cells. In such complex fluids, the cells are far too large to diffuse into the network structure of the superabsorbent material, and may instead adsorb onto the surfaces of the particles of superabsorbent material. The high osmotic pressure of partially swollen superabsorbent material can de-water the cells if they are in direct contact and this can lead to a nearly impermeable surface layer of cells surrounding the superabsorbent material, resulting in a severe reduction in the efficacy of the superabsorbent material. These factors suggest that the nature of the superabsorbent material for absorbing complex fluids such as menses should be different from the superabsorbent material used for absorbing simple fluids such as urine. Examples of other complex fluids include blood, runny bowel movements, and nasal discharge.

A further challenge in developing products into which superabsorbent materials are incorporated is the loss of absorbency under high loads caused by rigorous processing conditions. The act of processing materials, such as converting a material into a diaper absorbent core, tends to fracture superabsorbents. Prior to the development of inhomogeneously crosslinked polyacrylate superabsorbents, fracture was actually seen as desirable to soften the absorbent product. In fact, the deliberate breakage of polyacrylate superabsorbents was considered a means of softening the product. However, with the development of inhomogeneously crosslinked polyacrylates (shell-core materials), fracture during processing has become recognized as detrimental to absorbency, as discussed in U.S. Pat. No. 6,214,274.

There is a need or desire for an absorbent material that is capable of handling simple and complex fluids and can withstand rigorous processing conditions without losing absorbency under high loads.

SUMMARY OF THE INVENTION

In response to the discussed difficulties and problems encountered in the prior art, a new absorbent composite has been discovered.

The present invention is directed to superabsorbent material with a shell of surface crosslinks. This inhomogeneous crosslinking allows the bulk of the material to have high capacity while the shell prevents deformation under load. The disadvantage of the core/shell structure under rigorous process conditions where the shell is fractured negates the benefit of increased absorbent capacity under loads.

The absorbent composite of the invention includes an inhomogeneously crosslinked polyacrylate superabsorbent material coated with any of a variety of protective materials, such as cellulose fibers, with a variety of association agents to provide a "cushion" to protect the superabsorbent during processing. Following rigorous processing conditions, which can be simulated using the Ball-Mill Process described below, the Absorbency-Under-Load (AUL) (0.9 psi) of the superabsorbent is not degraded compared to the AUL of the superabsorbent prior to undergoing the rigorous process conditions. In some cases the 0.9 psi AUL is also enhanced by the coating compared to an uncoated superabsorbent material. This increase is believed to be due to the cushioning of the particle by the fiber on the surface. Fiber may be detached from the surface by ball-milling, so the protection for the coated particles may be slowly removed during processing.

The length of time of the ball-mill procedure can be varied, and 0.9 AULs measured to identify a maximum possible level of protection for possible process variations. The quantity or type of coating can then be modified such that the maximum absorbency occurs under standard converting conditions.

The material of this invention can also handle complex fluids which may be advantageous in certain product executions. More specifically, the coating can adsorb cells, tissue, and proteins, allowing the superabsorbent to effectively absorb the remaining fluid.

The absorbent composite of the invention can be made by combining an inhomogeneously crosslinked superabsorbent polymer, a protective, fibrous coating material, and an association medium. An example of a suitable coating material is cellulose powder. An example of a suitable association medium is water, since slightly wet superabsorbent polymer becomes sticky and, unexpectedly, continues to hold the coating even after drying. Water-soluble additives can also be added to the absorbent composite. With some of these soluble additives, fluid intake rate may increase or odor may be controlled, for example.

The absorbent composite of the invention can be used to make diapers, training pants, and incontinence products that are effective for runny bowel movements, and hyperthin feminine products for menses management, as well as paper towels and tissues that not only absorb more fluid but are also dry to the touch within minutes of absorbing fluid.

With the foregoing in mind, particular embodiments of the invention provide an absorbent composite that is capable of handling complex fluids and can withstand rigorous processing conditions without losing absorbency under high loads.

DEFINITIONS

Figure 1:
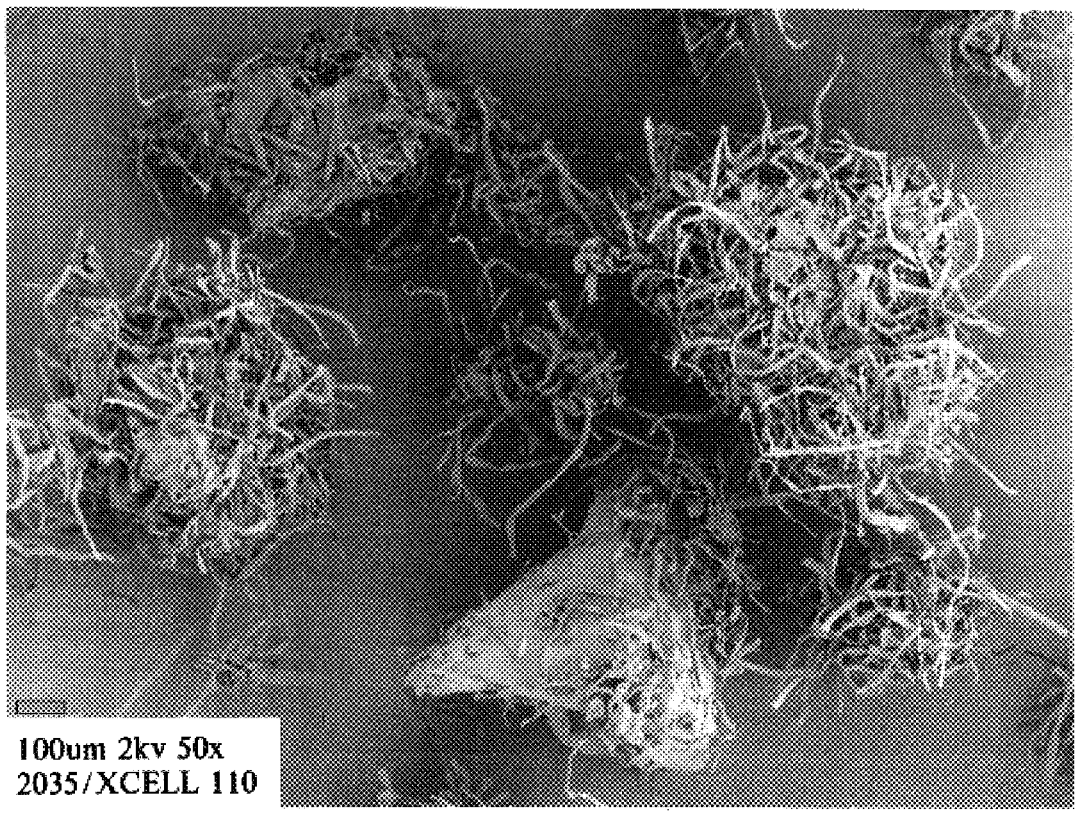
FIG. 1 illustrates several coated superabsorbent particles.

Within the context of this specification, each term or phrase below will include the following meaning or meanings.

"Absorbent material" refers to a material that is capable of absorbing or taking in a substance by cohesive, chemical, or molecular action.

"Adsorbent material" refers to a material that is capable of accumulating a substance on a surface of the material.

"Complex fluid" describes a fluid generally characterized as being a viscoelastic mixture including specific components having generally inhomogeneous physical and/or chemical properties. It is the inhomogeneous properties of the specific components that challenge the efficacy of a superabsorbent material in the handling of complex fluids, such as, for example, blood, menses, runny bowel movements, nasal discharges and the like. In contrast with complex fluids, simple fluids, such as, for example, urine, physiological saline, water and the like, are generally characterized as being Newtonian and including one or more components having generally homogeneous physical and/or chemical properties. As a result of having homogeneous properties, the one or more components of simple fluids behave substantially similarly during absorption or adsorption.

"Cover," "covers," "covering" or "covered" with regard to coating material is intended to indicate that the coating material extends over the surface of the material being covered to the extent necessary to realize many of the advantages of the absorbent composites prepared according to the present invention. Without desiring to be bound by theory, this includes situations where the coating material extends over at least about 20 percent of the surface of the material being covered; alternatively, over at least about 30 percent of the surface of the material being covered; alternatively, over at least about 40 percent of the surface of the material being covered; alternatively, over at least about 50 percent of the surface of the material being covered; alternatively, over at least about 60 percent of the surface of the material being covered; alternatively, over at least about 70 percent of the surface of the material being covered; alternatively, over at least about 80 percent of the surface of the material being covered; and finally, alternatively, over at least about 90 percent of the surface of the material being covered. The term "surface" and its plural generally refer herein to the outer or the topmost boundary of an object.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 are designated "wettable" or hydrophilic, while fibers having contact angles greater than 90 are designated "non-wettable" or hydrophobic.

"Inhomogeneously crosslinked" refers to an increased crosslinked density in a region of a superabsorbent particle. A particularly preferred form of inhomogeneous crosslinking is an increased crosslink density at the surface of the particle forming a shell/core structure.

"Intimate association" and other similar terms are intended to encompass configurations including the following: those where at least a portion of the surface of at least one particle of a layer of coating material is in contact with a portion of the surface of at least one particle of superabsorbent material; and/or those where at least a portion of the surface of at least one particle of a layer of coating material is in contact with a portion of the surface of at least one other particle of a layer of coating material.

"Particle," "particles," "particulate," "particulates" and the like, refer to a material that is generally in the form of discrete units. The particles can include granules, pulverulents, powders or spheres. Thus, the particles can have any desired shape such as, for example, cubic, rod-like, polyhedral, spherical or semi-spherical, rounded or semi-rounded, angular, irregular, etc. Shapes having a large greatest dimension/smallest dimension ratio, like needles, flakes and fibers, are also contemplated for use herein. The use of "particle" or "particulate" may also describe an agglomeration including more than one particle, particulate or the like.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Relatively high-density, compacted core" refers to an absorbent structure having a density greater than 0.1 grams per cubic centimeter.

"Relatively low-density core" refers to an absorbent structure having a density less than or equal to 0.1 grams per cubic centimeter.

"Resilient" refers to a material that is capable of being compressed and returning to an original shape or position after having been compressed. A highly resilient material will recover at least 90% of its original dimension after a compression similar to that experienced in normal use. A resilient material will recover at least 60% of its original shape after a compression similar to that experienced in normal use. A somewhat resilient material will recover at least 30% of its original shape after a compression similar to that experienced in normal use.

"Superabsorbent," "superabsorbent material" and the like are intended to refer to a water-swellable, water-insoluble organic or inorganic material capable, under the most favorable conditions, of absorbing at least about 10 times its weight and, preferably, at least about 15 times its weight in an aqueous solution containing 0.9 weight percent of sodium chloride. Such materials include, but are not limited to, hydrogel-forming polymers which are alkali metal salts of: poly(acrylic acid); poly(methacrylic acid); copolymers of acrylic and methacrylic acid with acrylamide, vinyl alcohol, acrylic esters, vinyl pyrrolidone, vinyl sulfonic acids, vinyl acetate, vinyl morpholinone and vinyl ethers; hydrolyzed acrylonitrile grafted starch; acrylic acid grafted starch; maleic anhydride copolymers with ethylene, isobutylene, styrene, and vinyl ethers; polysaccharides such as carboxymethyl starch, carboxymethyl cellulose, methyl cellulose, and hydroxypropyl cellulose; poly(acrylamides); poly(vinyl pyrrolidone); poly(vinyl morpholinone); poly(vinyl pyridine); and copolymers and mixtures of any of the above and the like. The hydrogel-forming polymers are preferably lightly cross-linked to render them substantially water-insoluble. Cross-linking may be achieved by irradiation or by covalent, ionic, van der Waals attractions, or hydrogen bonding interactions, for example. A desirable superabsorbent material is a lightly cross-linked hydrocolloid. Specifically, a more desirable superabsorbent material is a partially neutralized polyacrylate salt.

These terms may be defined with additional language in the remaining portions of the specification.

DETAILED DESCRIPTION OF THE PRESENTLY PREFERRED EMBODIMENTS

The present invention is directed to an absorbent composite that is capable of withstanding rigorous processing conditions without losing absorbency under high loads and is also capable of handling complex fluids.

The absorbent composite includes at least one particle of superabsorbent material (SAM) covered with at least one particle of coating material. More specifically, the absorbent composite includes an inhomogeneously crosslinked superabsorbent polymer, preferably covered by a shell of surface crosslinks, and coated with a protective fibrous coating material and an association medium.

The inhomogeneous crosslinking allows the bulk of the material to have high capacity while the more densely crosslinked shell prevents deformation under load. The act of processing the material, for example converting the material into a diaper absorbent core, tends to break the cross-linked surface, exposing the soft interior of the particle and, as a consequence, reducing the absorbency under load. This processing can be simulated using the Ball-Mill Test, described below. Following exposure to the Ball Mill Test, the Absorbency-Under-Load (0.9 psi) for the as received superabsorbent fell, as expected. In contrast, the coated superabsorbent was found to either maintain the starting superabsorbent value or even increase compared to the starting polymer or composite. This result is believed to be due to the cushioning of the particle by the coating on the surface of the coated particles of this invention.

Using the Ball Mill Test, an optimum coating level can be identified for protection of the superabsorbent in simulated current processing steps. For example, the length of time of the Ball Mill Test can be varied to correspond to a specific process. Measuring the ALL serves to identify a maximum possible level of protection for possible process variations. After reviewing the results of the Ball Mill Test, the quantity or type of coating can be customized such that maximum absorbency occurs under standard converting conditions.

Superabsorbent materials employed in the present invention suitably should be able to absorb a liquid under an applied load as well as under zero load. For purposes of this application, the ability of a superabsorbent material to absorb a liquid under an applied load and thereby perform work is quantified as the Absorbency Under Load (AUL) value. The AUL value is expressed as the amount (in grams) of an approximately 0.9 weight percent saline (sodium chloride) solution absorbed by about 0.160 grams of superabsorbent material when the superabsorbent material is under a load. Common loads, further described hereinbelow, include those of about 0.01 pound per square inch, 0.29 pound per square inch, 0.57 pound per square inch, and about 0.90 pound per square inch. The uncoated, starting superabsorbent materials suitable for use herein desirably are stiff-gelling superabsorbent materials having an AUL value under a load of about 0.3 pound per square inch of at least about 7 grams/gram (g/g); alternatively, at least about 9 g/g; alternatively, at least about 15 g/g; alternatively, at least about 20 g/g; alternatively, at least about 24 g/g; and, finally, alternatively, at least about 27 g/g.

The method by which AUL is determined is set forth in greater detail in the Test Methods section. The AUL is thought to be a function of the following factors: (1) gel stiffness while swelling, (2) ability to imbibe the fluid by osmotic and internal electrostatic repulsion forces, (3) surface wettability of the superabsorbent material and (4) particle size distribution when wet. Although known to those skilled in the art, the AUL of a superabsorbent material is further described in U.S. Pat. Nos. 5,147,343 and 5,601,542, as well as European Publication No. 0339461 B1, the disclosure of each of which is incorporated herein by reference to the extent that each is consistent (i.e., does not conflict) with the present specification.

Useful superabsorbent materials, generally developed primarily for absorbing simple fluids such as urine, are typically available from various commercial vendors, such as, for example, Dow Chemical Company or Stockhausen, Inc. One commercial example of a suitable superabsorbent material includes FAVOR SXM 880, available from Stockhausen Inc., Greensboro, N.C., U.S.A. Another is DRYTECH 2035, available from Dow Chemical Company, Midland, Mich., U.S.A. The absorbent composites of the invention suitably include between 30% and 97% superabsorbent polymer (SAM), or between 50% and 92% SAM, or between 60% and 90% SAM.

Although a complex fluid is generally characterized herein as including specific components having inhomogeneous properties, each specific component of a complex fluid generally has homogeneous properties. Consider for example a hypothetical complex fluid having three specific components: red blood cells, blood protein molecules and water molecules. Upon examination, one skilled in the art could easily distinguish between each of the three specific components according to their generally inhomogeneous properties. Moreover, when examining a particular specific component such as the red blood cell component, one skilled in the art could easily recognize the generally homogeneous properties of the red blood cells.

A wide variety of materials capable of selectively removing at least a portion of an amount of at least one specific component of a complex fluid can be suitably employed as the superabsorbent material of the present invention. It is desired, however, to employ superabsorbent materials in particle form capable of absorbing large quantities of fluids, such as water, and of retaining such absorbed fluids under moderate pressures. It is even more desired to use relatively inexpensive and readily obtainable superabsorbent materials that have typically been developed primarily to absorb simple fluids.

The superabsorbent material used in the invention is inhomogeneously crosslinked, also known as a core/shell superabsorbent. Examples of superabsorbent materials suitable for use in the present invention are commercially available from Stockhausen Inc., Greensboro, N.C., U.S.A., and also from Dow Chemical Company of Midland, Mich., U.S.A. Suitable superabsorbent materials are also taught in U.S. Pat. Nos. 6,239,230 and 5,447,727, both of which are hereby incorporated by reference.

Suitably, the superabsorbent material is in the form of particles which, in the unswollen state, have maximum cross-sectional diameters ranging between about 50 and about 3,000 microns; desirably, between about 100 and about 1000 microns; more desirably, between about 200 and about 650 microns; as determined by sieve analysis according to American Society for Testing Materials Test Method D-1921. It is understood that the particles of superabsorbent material may include solid particles, porous particles, or may be agglomerated particles including many smaller particles agglomerated into particles falling within the described size ranges.

As mentioned, the coated material includes a coating material that provides resiliency to the superabsorbent particle as well as having the ability to remove a component of a complex fluid. A wide variety of natural and synthetic materials, capable of selectively removing at least a portion of an amount of at least one specific component of a complex fluid, can be employed as the coating material of the present invention. Suitable coating materials therefore include adsorbent and/or absorbent material. It is, of course, desired to use coating materials that are inexpensive, readily available and safe—important attributes for a material used in the disposable absorbent articles described herein. Illustrative examples of coating material suitable for use in the present invention include particles of hydrophilic material. Examples of hydrophilic material suitable for use as coating material include, but are not limited to, cellulosic materials, both natural and synthetic, such as wood pulp and products made from it such as powdered cellulose, and non-woody cellulose materials such as cotton, linen, jute, abaca, ixtl and the like, and products made from them such as cotton linters and floc; regenerated cellulose such as rayon, cupram, lyocell and the like; and cellulose derivatives such as hydroxypropyl cellulose, hydroxyethyl cellulose, ethyl cellulose, cellulose acetate and the like. One commercial example of a particularly suitable cellulose powder is EXCEL 110, a fibrillated birch pulp, available from Functional Foods, located in Elizabethtown, N.J. A particularly desired coating material is microcrystalline cellulose powder. One commercial example of a suitable microcrystalline cellulose is AVICEL, available from FMC Corporation in Philadelphia, Pa. Another suitable cellulose material is SULFATATE HJ, a hardwood pulp available from Rayonier Inc., Jesup, Ga., U.S.A. When small cellulose fibers are used as the coating, the resulting coated superabsorbent is "fuzzy" and will stay in place within an absorbent structure, greatly reducing superabsorbent shakeout. The fibers also unexpectedly have been found to impart a resilient character to the coated particulate which protects the superabsorbent during processing under rigorous conditions.

Alternate non-fibrous coatings include ZEOFREE 5175A, a granulated, precipitated silica commercially available from J. M. Huber, Havre de Grace, Md., U.S.A.; SILKLEER 25 M, a fine particle, mined, processed perlite; and RYOLEX 39, a coarser, mined processed perlite, the SILKLEER and RYOLEX available from Silbrico Corporation, Hodgkins, Ill., U.S.A.

The coating may also be receptive to microwave or radio frequency (RF) electromagnetic radiation. These energy receptive coatings could function to absorb microwaves and, through dielectric heating, melt or soften binder fibers present in the web, thus providing integrity to the web. Such energy receptive coatings may be, for example, carbon black, magnetite, silicon carbide, calcium chloride, zircon, ferrite, tin oxide, alumina, magnesium oxide, and titanium dioxide. The dielectric heating allows the matrix polymer to reach its melting temperature much more rapidly than it would without the energy receptive coating and allows fiber bonding in the web to occur at a faster rate than without the coating.

Coatings such as ZEOFREE, SILKLEER, and RYOLEX offer increased surface area and the ability to pick up specific materials such as blood, menses, and bowel movements. By blending the materials it is expected to get the best of both material properties of the coatings. Also by blending the coatings the silicate in the particles not only sticks to the superabsorbent but also to the pulp fibers attached to the superabsorbent. Combinations of fibrous and non-fibrous coatings, for example, EXCEL 110 and ZEOFREE 5175A, have been found to show the higher adsorptivity typical of non-fibrous coatings combined with the resiliency of fibrous coatings.

More particularly, when a protective, fibrous coating material used in the present invention is coated onto the superabsorbent, the fibers of the coating material are preferably attached to the superabsorbent in such a way that at least one end of the fiber is oriented essentially perpendicular to the superabsorbent particle. Orientation of the fibers is very important. As shown in FIG. 1, the full length of the fibers need not project straight out from the superabsorbent, that is, the end of the fibers attached to the superabsorbent sticks straight out while the opposite end of the fibers may be oriented in virtually any position. Suitably, the fibers extend from the outer shell of the superabsorbent at a substantially perpendicular angle, namely an angle of between about 65 degrees and about 90 degrees, or between about 80 degrees and about 90 degrees. The fibers in the composite of the invention are not wrapped around the superabsorbent. Longer fibers may appear to be wrapped, but even the longer fibers stick straight out from the superabsorbent at least at the end attached to the superabsorbent.

Chemically stiffened fibers may also be included in the composite of the invention, as long as the fibers stick straight out from the superabsorbent and do not substantially wrap the superabsorbent. As used herein, the term "chemically stiffened, cellulosic fibers" means cellulosic fibers which have been stiffened by chemical means to increase stiffness of the fibers under both dry and aqueous conditions. Such means include the addition of chemical stiffening agents which, for example, coat and/or impregnate the fibers. Such means also include the stiffening of the fibers by altering the chemical structure of the fibers themselves, e.g., by cross-linking polymer chains.

It should be further noted that the present invention is not limited to the use of only one coating material, but can also include mixtures of two or more coating materials. Although hydrophilic materials have been indicated as being suitable for use as coating materials in the present invention, one skilled in the art would readily appreciate the possibility of treating the surfaces of hydrophobic materials by an appropriate known method to render the hydrophobic materials more or less hydrophilic. As previously indicated, the coating material is in particulate form; consequently, it is understood that the particles of coating material may include solid particles, porous particles, fibers, or may be an agglomeration of more than one particle of coating material.

In various embodiments of the present invention, the intimate association of a coating material with a superabsorbent material is achieved with the use of an association agent, or association media. The association agent usually includes substances that can be applied in liquid or semi-liquid form to either the superabsorbent material or the coating material. The term "applied" as used herein is intended to include situations where: at least a portion of the surface of at least one particle of superabsorbent material has an effective amount of association agent on it to facilitate adherence, via mechanical and/or chemical bonding, of at least that portion of the surface of the superabsorbent material to a portion of the surface of at least one particle of coating material; at least a portion of the surface of at least one particle of coating material has an effective amount of association agent on it to facilitate adherence, via mechanical and/or chemical bonding, of at least that portion of the surface of the coating material to a portion of the surface of at least one particle of superabsorbent material; and/or at least a portion of the surface of at least one particle of coating material has an effective amount of association agent on it to facilitate adherence, via mechanical and/or chemical bonding, of at least that portion of the surface of the coating material to a portion of the surface of at least one other particle of coating material. Desirably, the association agent is applied to the selected material in an amount of from about 2 parts of association material per part of coating to 0.1 part of association material to 1 part of coating.

The selection of a particular association agent can be made by one skilled in the art and will typically depend upon the chemical composition of the materials to be maintained in intimate association with one another. Desirably, the association agent is suitable for use in applications involving human contact. Thus, the association agent should be non-toxic and non-irriatating to humans. An association agent suitable for use in the present invention is typically prepared by the formation of a liquid or semi-liquid capable of being generally uniformly atomized. In particular, a solution, dispersion or emulsion including at least one of the association agents identified herein may be prepared. Although the association agent is described herein as being applied as finely atomized droplets, it may be applied to the selected material by any other method such as by spraying in liquid or semi-liquid form, spraying and blowing in the form of steam, and the like.

Several types of association agent are capable of being employed in the present invention. Illustrative association agents suitable for use in various embodiments of the present invention include, for example: water; volatile organic solvents such as alcohols; aqueous solutions of film-forming materials such as dried milk, lactose, soluble soy protein, and casein; synthetic adhesives such as polyvinyl alcohol; and mixtures thereof. The presence of water in the association agent is particularly effective in predisposing the superabsorbent material to wetting. In an optional subsequent drying process, the water may be evaporated and therefore not part of the final coated particle.

As used herein, the phrase "absorbent article" refers to devices which absorb and contain body fluids, and more specifically, refers to devices which are placed against or near the skin to absorb and contain the various fluids discharged from the body. The term "disposable" is used herein to describe absorbent articles that are not intended to be laundered or otherwise restored or reused as an absorbent article after a single use. Examples of such disposable absorbent articles include, but are not limited to: health care related products including ostomy products, surgical drapes, gowns, and sterilization wraps; personal care absorbent products such as feminine hygiene products, diapers, training pants, incontinence products and the like; as well as facial tissues, and absorbent liners suitable for food contact, such as poultry and meat pads.

Disposable absorbent articles such as, for example, many of the personal care absorbent products, typically include a fluid pervious topsheet, a liquid impervious backsheet joined to the topsheet and an absorbent core positioned between the topsheet and the backsheet. Disposable absorbent articles and components thereof, including the topsheet, backsheet, absorbent core and any individual layers of these components, generally have a body-facing surface and a garment-facing surface. As used herein, "body-facing surface" refers to that surface of the article or component which is intended to be worn toward or placed adjacent to the body of the wearer, while the "garment-facing surface" is on the opposite side and is intended to be worn toward or placed adjacent to the wearer's undergarments or other appropriate clothing when the disposable absorbent article is worn.

The absorbent composites of the present invention are suitable for use in a variety of disposable absorbent articles. In general, the absorbent composites may be used in a manner similar to that in which other absorbent composites have been used: for example, in laminates, in relatively high density cores (i.e., compacted cores, calendered cores, densified cores, etc.), or in relatively low density cores (i.e., not compacted, for example, air-laid cores). However, the absorbent composites of the present invention can provide certain advantages over conventional absorbent composites.

In particular, the absorbent composites of the present invention demonstrate an improved efficacy in the handling of complex fluids, such as menses and runny bowel movements. More particularly, the absorbent composites of the present invention demonstrate an improved efficacy in the handling of menses. As a result of this improved efficacy, the incorporation of the absorbent composite of the present invention into feminine hygiene products such as, for example, sanitary napkins and panti-liners, results in a user of such products experiencing a sense of increased dryness. In addition, feminine hygiene products incorporating the absorbent composites of the present invention may be made thinner while being able to absorb substantially similar amounts of menses as is absorbed by much thicker feminine hygiene products that do not contain the absorbent composites of the present invention. For example, the absorbent material of the present invention can be used to produce absorbent structures having a thickness of less than 10 millimeters (mm), or less than 8 mm, or less than 6 mm.

The absorbent composite may be prepared in a manner similar to fluidized bed coating processes. As an example of one process, at least one particle of a coating material is suspended in a fluidized bed coating apparatus that creates a strong upward current or stream of fluidizing gas, usually air, typically at an inlet temperature approximating that of room temperature. The strong upward current or stream of fluidizing gas moves the coating material upward until the coating material passes out of the upward stream and passes downward in a fluidized condition countercurrent to the upward stream of fluidizing gas. The coating material may re-enter the upward-moving stream of fluidizing gas. While in the upward-moving stream, the coating material passes through a zone where an association agent is applied to the coating material.

After the association agent is applied to the coating material, at least one particle of superabsorbent material is introduced into the apparatus. A strong upward current or stream of fluidizing gas, usually air, optionally at an elevated inlet temperature (i.e., a temperature typically above room temperature), moves the coating material and the superabsorbent material upward until the coating material and the superabsorbent material pass out of the upward stream and pass downward in a fluidized condition countercurrent to the upward stream of fluidizing gas. The coating material and the superabsorbent material may re-enter the upward-moving stream of fluidizing gas until an absorbent composite is formed. It is typically after the association agent is applied that the coating material comes into intimate association with the superabsorbent material to form the absorbent composite.

The absorbent composite of the invention may also be prepared by a process in which at least one particle of a superabsorbent material is suspended in a fluidized bed coating apparatus that creates a strong upward current or stream of fluidizing gas, usually air, typically at an inlet temperature approximating that of room temperature. The strong upward current or stream of fluidizing gas moves the superabsorbent material upward until the superabsorbent material passes out of the upward stream and passes downward in a fluidized condition countercurrent to the upward stream of fluidizing gas. The superabsorbent material may re-enter the upward-moving stream of fluidizing gas. While in the upward-moving stream, the superabsorbent material passes through a zone where an association agent is applied to the superabsorbent material.

Alternatively, it may be convenient to wet the superabsorbent with the association material and then charge the fluidized bed with the pre-wetted superabsorbent.

After the association agent is applied to the superabsorbent material, at least one particle of coating material is introduced into the apparatus. A strong upward current or stream of fluidizing gas, usually air, optionally at an elevated inlet temperature, moves the coating material and the superabsorbent material upward until the coating material and the superabsorbent material pass out of the upward stream and pass downward in a fluidized condition countercurrent to the upward stream of fluidizing gas. The coating material and the superabsorbent material may re-enter the upward-moving stream of fluidizing gas until an absorbent composite is formed. It is typically after the association agent is applied that the coating material comes into intimate association with the superabsorbent material to form the absorbent composite.

The absorbent composite of the invention may also be prepared by a process in which at least one particle of coating material and at least one particle of superabsorbent material are suspended in a fluidized bed coating apparatus that creates a strong upward current or stream of fluidizing gas, usually air, typically at an inlet temperature approximating that of room temperature. The strong upward current or stream of fluidizing gas moves both the coating material and the superabsorbent material upward until the coating material and the superabsorbent material pass out of the upward stream and pass downward in a fluidized condition countercurrent to the upward stream of fluidizing gas. The coating material and the superabsorbent material may re-enter the upward-moving stream of fluidizing gas. While in the upward-moving stream, the coating material and the superabsorbent material pass through a zone where an association agent is applied to both the coating material and superabsorbent material.

After the association agent is applied, the strong upward-moving stream of fluidizing gas, usually air, optionally at an elevated inlet temperature, moves the coating material and the superabsorbent material upward until the coating material and the superabsorbent material pass out of the upward stream and pass downward in a fluidized condition countercurrent to the upward stream of fluidizing gas. The coating material and the superabsorbent material may re-enter the upward-moving stream of fluidizing gas until an absorbent composite is formed. It is typically after the association agent is applied that the coating material comes into intimate association with the superabsorbent material to form the absorbent composite.

Figure 2:
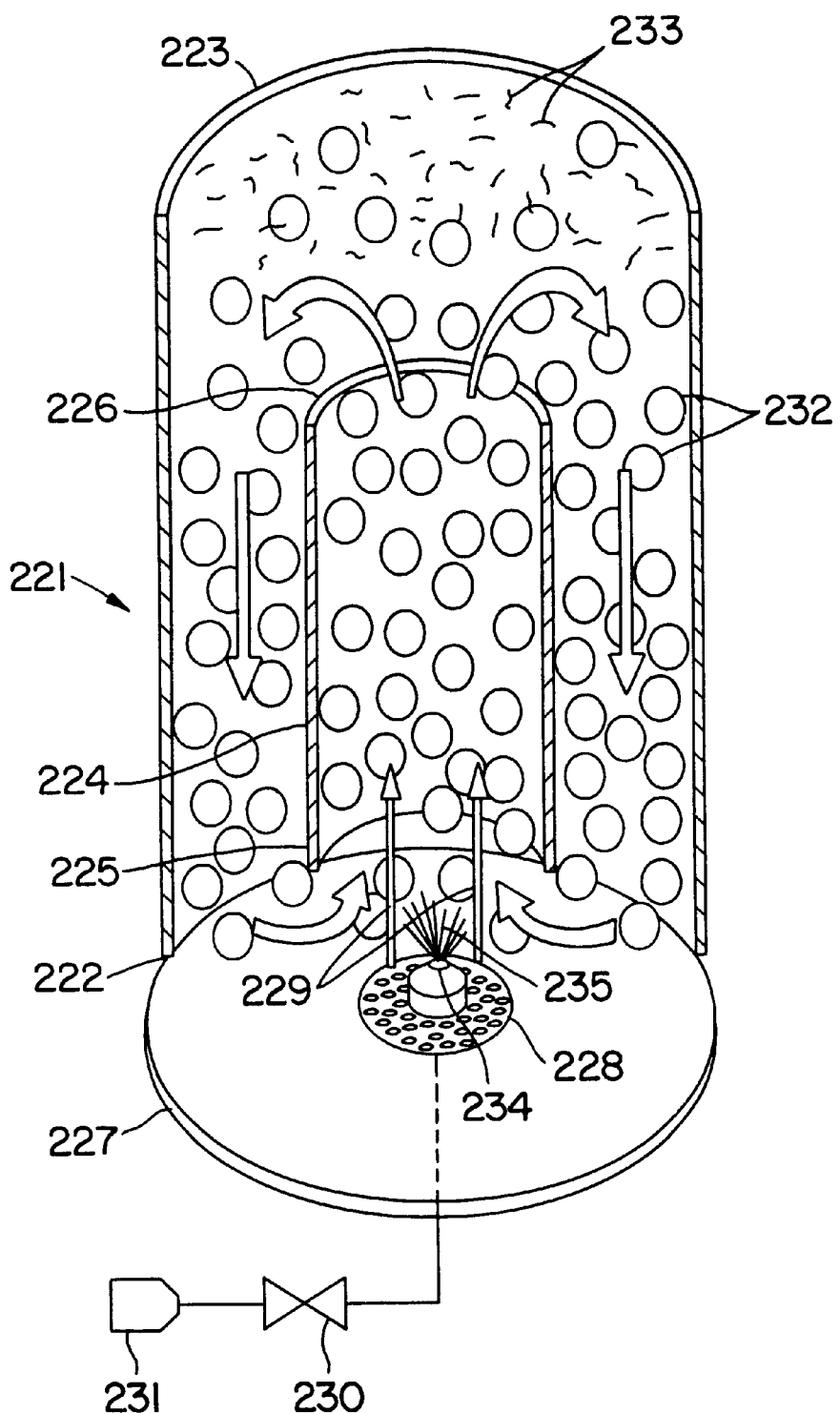
FIG. 2 illustrates a representative fluidized bed coating apparatus.

Typically, a fluidized bed coating apparatus similar to that illustrated in FIG. 2 can be utilized to form the absorbent composite of the invention. Referring to FIG. 2, a generally vertically-mounted, generally cylindrical chamber (221) is open at chamber proximal end (222) and closed at chamber distal end (223). The chamber (221) is optionally provided with an inner chamber (224) that has a diameter less than that of the chamber. The inner chamber (224) is open at both inner chamber proximal end (225) and inner chamber distal end (226). The chamber proximal end (222) is fitted with a plate (227) that has a porous area (228) that generally matches the diameter of the inner chamber (224). The inner chamber (224) is positioned a distance above the plate (227) and is generally aligned along the vertical axis of the chamber (221). Through the porous area (228) is provided an upward current or stream (229) of fluidizing gas, usually air, typically at an inlet temperature approximating that of room temperature, such as from a valve (230) from a source of compressed gas (231). The upward-moving stream (229) of fluidizing gas generally flows through the inner chamber (224) by entering through the inner chamber proximal end (225) and exiting through the inner chamber distal end (226).

As described in one of the previously mentioned processes, at least one particle of coating material (233) is introduced into the chamber (221). The upward-moving stream (229) of fluidizing gas is adjusted so as to provide a fluid-like flow to the coating material (233). The upward-moving stream (229) of gas moves the coating material (233) upward until the coating material passes out of the upward stream and passes downward in a fluidized condition countercurrent to the upward-moving stream of fluidizing gas. The coating material (233) may re-enter the upward-moving stream (229) of fluidizing gas. While in the upward-moving stream, the coating material passes through a zone where an association agent (235) is applied to the coating material (233). This zone is generally located in the vicinity of a sprayer means (234) positioned near the center of the plate (227).

After the association agent is applied to the coating material (233), at least one particle of superabsorbent material (232) is introduced into the chamber (221). If necessary, the upward-moving stream (229) of gas is adjusted so as to provide a fluid-like flow to the superabsorbent material (232) and the coating material (233).

After introduction of the superabsorbent material (232), the inlet temperature of the upward-moving stream (229) of fluidizing gas is optionally elevated to a temperature in excess of room temperature. The cyclic flow of the superabsorbent material (232) and the coating material (233) is generally allowed to continue in the chamber (221) until the coating material comes into intimate association with the superabsorbent material to form the absorbent composite of the invention. The absorbent composite is then recovered or removed from the chamber (221).

The absorbent composite so formed includes at least one particle of superabsorbent material covered with at least a first layer of at least one particle of coating material. The coating material of the first layer is in intimate association with and covering the surface of the superabsorbent material.

While other processes may be used to form the absorbent composite of the invention, the fluidized bed coating process described above is relatively mild in its effect on the superabsorbent material being brought into intimate association with the coating material and is therefore less damaging to the microstructure of the superabsorbent material as compared to other processes. Although discussed in terms of being formed in a fluidized bed coating process, the absorbent composite may also be formed using a variety of other processes incorporating, for example, a V-shell blender or other apparatus that is relatively mild in its effect on the superabsorbent material.

Optionally, after formation, the absorbent composite may remain in the apparatus and subject to the strong upward current or stream of fluidizing gas at an elevated temperature until the moisture content of the absorbent composite is less than that which would support the growth of microorganisms. While not desiring to be bound by theory, it is believed that to minimize the likelihood of the growth of microorganisms, the moisture content of the absorbent composite should be about 25 percent or less by weight; desirably, about 15 percent or less by weight; more desirably, about 10 percent or less by weight; and most desirably, about 5 percent or less by weight. Although the processes described herein have been described as optionally drying an absorbent composite in the apparatus, the optional drying of an absorbent composite could be accomplished either in the apparatus or out of the apparatus according to any of a number of other drying processes known to those skilled in the art.

Depending on the intended use of the absorbent composite, it may be desired to add a second layer of at least one particle of coating material to an absorbent composite. The second layer of coating material, as well as any subsequent additional layer of coating material, is added in generally the same manner as is a first layer of coating material according to the at least one of the processes described herein.

Although previously described herein as having a one- or two-layered configuration, it is also within the present invention to form absorbent composites having more than two layers. Consequently, it is within the scope of the present invention to form absorbent composites having a single layer of coating material or absorbent composites having two or more layers of coating material in a variety of multi-layered configurations with each layer including one or more coating materials.

Although previously described herein, it is also within the present invention to form absorbent composites having mixtures of coating materials in which the single layer or the two or more layers of coating material comprises one or more components. Consequently, it is within the scope of the present invention to form absorbent composites having a variety of single layer or multilayered configurations with each layer including one or more coating materials.

An absorbent composite of the present invention suitably has a weight ratio, based on the total weight of the superabsorbent material and the coating material in the absorbent composite, of superabsorbent material to coating material of from about 30:70 to about 97:3; alternatively, from about 40:60 to about 80:20; and finally, alternatively, from about 60:40 to about 70:30. In addition, an absorbent composite of the present invention suitably should be able to retain a complex fluid. The ability of an absorbent composite of the present invention to retain a complex fluid is quantified herein as the complex fluid retention capacity (CFRC). The complex fluid retention capacity is a quantification of the amount of complex fluid that an absorbent composite retains after a force has been applied. The amount of complex fluid retained is calculated as a gram per gram retention. Suitably, an absorbent composite of the present invention has a complex fluid retention capacity, as further defined hereinbelow, of between 0 and about 30; alternatively, of between about 5 and about 30; alternatively, of between about 10 and about 30; alternatively, of between about 12 and about 30; alternatively, of between about 13 and about 30; alternatively, of between about 15 and about 30; and finally, alternatively, of between about 18 and about 30 g/g.

As previously mentioned, current commercially available, mass-produced superabsorbent materials interact with complex fluids, such as menses, in a very ineffective manner. Red blood cells (constituting approximately 30 to 50 percent of typical menses samples) can adsorb onto the surface of a particle of superabsorbent material and coat the surface of the particle of superabsorbent material, both hindering the flow of fluid to the surface and providing a physical restraint, thus preventing swelling of the particle of superabsorbent material. Even in the absence of red blood cells, blood proteins have been observed to cause a similar, though somewhat less striking, reduction in capacity due to essentially the same cause—deposition of proteins on the surface of a particle of superabsorbent material. Menses, for example, contains, inter alia, mucus or mucin materials. These mucin materials can be de-watered into an essentially liquid-impermeable barrier on the surface of a particle of superabsorbent material resulting in a striking reduction in retention capacity.

The relatively larger components—generally considered as those components having a diameter greater than about five microns—of a complex fluid can adsorb onto and coat the surface of a particle of superabsorbent material, thus mitigating the efficacy of a superabsorbent material in the handling of a complex fluid. Desirably, an embodiment of the absorbent composite of the present invention demonstrates an improved efficacy in the handling of a complex fluid as a result of the coating material substantially inhibiting those components of a complex fluid having a diameter of greater than about five microns from being adsorbed onto the surface of the superabsorbent material of the absorbent composite.

Since adsorption of cells and molecules generally takes place at the surface of a coating material, an absorbent composite having either increased surface area of a coating material or increased surface activity of the coating material toward the adsorption of specific cells and molecules would typically increase the retention capacity of the superabsorbent material by delivering fewer of the interfering substances to the surface of the superabsorbent material.

Regardless of the surface area, a surface can be made more active, and thus more attractive to specific components of a complex fluid by chemical modification. A particularly simple and inexpensive method of modifying the surface activity of a material is to add a cationic debonding agent. Typical cationic debonding agents include quaternary amino compounds such as, for example, a quaternary ammonium salt of a fatty acid. As is well known to those who process wood pulp fibers, an aqueous solution of a debonding agent will spontaneously coat a cellulose surface. In the case of a cationic debonding agent, the cellulose surface will then become positively charged and will more effectively adsorb negatively charged red blood cells and blood proteins. A cellulose surface could also be directly derivatized, for example, by reaction to form diethylamino cellulose, a well known and easily prepared positively charged derivative. Again, the positive charge on the derivatized cellulose surface will more effectively remove cells and proteins from blood and menses.

Test Methods

Capacity and absorbency are calculated based on gram of fluid per gram of superabsorbent weight basis where the superabsorbent content is determined by sulfated ash procedure or other suitable method. The coating amount is not considered in the calculation of capacity and is assumed to be negligible. In the case where the coating is expected to absorb more than about 2 g/g this may be included in the absorbency of the coated particle. Most materials are typically screened to a given particle size distribution prior to testing AUL or CRC as described below. In the case of coated superabsorbents, often the coatings interfere with the ability to sieve the materials as they tend to entangle or stick to each other. In this case, the coated superabsorbents are tested in an as is particle size distribution or other defined particle size distribution. Also, the test methods typically have a given weight of test material to be used. For the coated superabsorbents this is the weight of the coated superabsorbent, not the weight of the superabsorbent component that is used. For example, in the AUL test, 0.160 grams of coated superabsorbent is used, but capacity was calculated based on grams of fluid per grams of superabsorbent component.

Analytical Techniques for Component Analysis

Various conventional techniques may be employed to determine the quantitative amount of superabsorbent material within a test sample. Suitable analytical techniques include, for example, a sulfated ash measurement method, such as described in Vogel's Textbook of Quantitative Inorganic Analysis, Fourth Edition, revised by J. Bassett, R. C. Denney, G. H. Jeffery, J. Mendham, Longman Inc., 1978, pp. 479–481. Another suitable technique would be an ion exchange method (e.g. sodium ion exchange), such as described in Treatise on Analytical Chemistry, Volume 1, edited by I. M. Kolthoff and Phillip J. Elving, Interscience Publishers, Inc., 1961, pp. 345–350. Further suitable techniques include atomic absorption methods, such as described in Vogel's Textbook of Quantitative Inorganic Analysis, Fourth Edition, revised by J. Bassett, R. C. Denney, G. H. Jeffery, J. Mendham, Longman Inc., 1978, pp. 810–845. The Encyclopedia of Industrial Chemical Analysis, Volume 18, edited by Foster Dee Snell and Leslie S. Ettre, Interscience Publishers, Inc., division of John Wiley & Sons, 1973, at pp. 207–259 further describes well-known, conventional techniques for quantitatively measuring the amount of sodium within a sample.

In the analyses conducted for the purposes of the present Examples, the quantitative determinations of superabsorbent content were made by a sulfated ash procedure. The chemical compositions of the superabsorbent polymers employed in the Examples included particular, known proportions of sodium. This technique measured the quantitative amounts of sodium and then employed the resultant measurements to derive the associated, corresponding amounts of superabsorbent polymer.

In particular, the test samples of the coated superabsorbent particles were burned over a Fischer burner and the ash treated with sulfuric acid. The sulfuric acid was driven off over the burner and then the samples placed in a muffle oven at 850 degrees Celsius for one hour. The percentage of superabsorbent material (SAM) present in the original samples was then calculated using the following equation:

% Carboxyl Salt Polymer=$(A)*(F)*(100)/(C)$ where (A)=mass of sulfated ash
(C)=mass of sample
(F)=SAM factor=1.96 for DRYTECH 2035; 1.92 for FAVOR SXM 880.

The SAM factor is determined by running the sulfated ash procedure on a given superabsorbent without coating to determine the grams of superabsorbent per gram of ash. Typical range for the SAM factor is 1.9 to 2.1 for conventional sodium-based polyacrylate superabsorbents.

For coated superabsorbents coated only with cellulose, the coating level was determined by difference.

For coated superabsorbents with silicates or a combination of a silicate and cellulose the percentage of silicate as $SiO_2$ was calculated from the percent silicon as determined by inductively coupled plasma. If the material contained both the silicate and a cellulose coating, the cellulose coating was determined by difference. It will be readily appreciated that articles made in accordance with the present invention may contain superabsorbent materials and coatings having chemical compositions different than that of the coated superabsorbent materials employed in the Examples. Such different superabsorbents may not contain sodium but would contain some other characteristic chemical component. Accordingly, the selected analytical technique for quantitatively measuring the amount of superabsorbent or coating material may need to be adjusted to target the particular characteristic component present in those compositions. The manner of such adjustment would be readily apparent to persons of ordinary skill in the analytical arts.

Absorbency Under Load (AUL)

Figure 3:
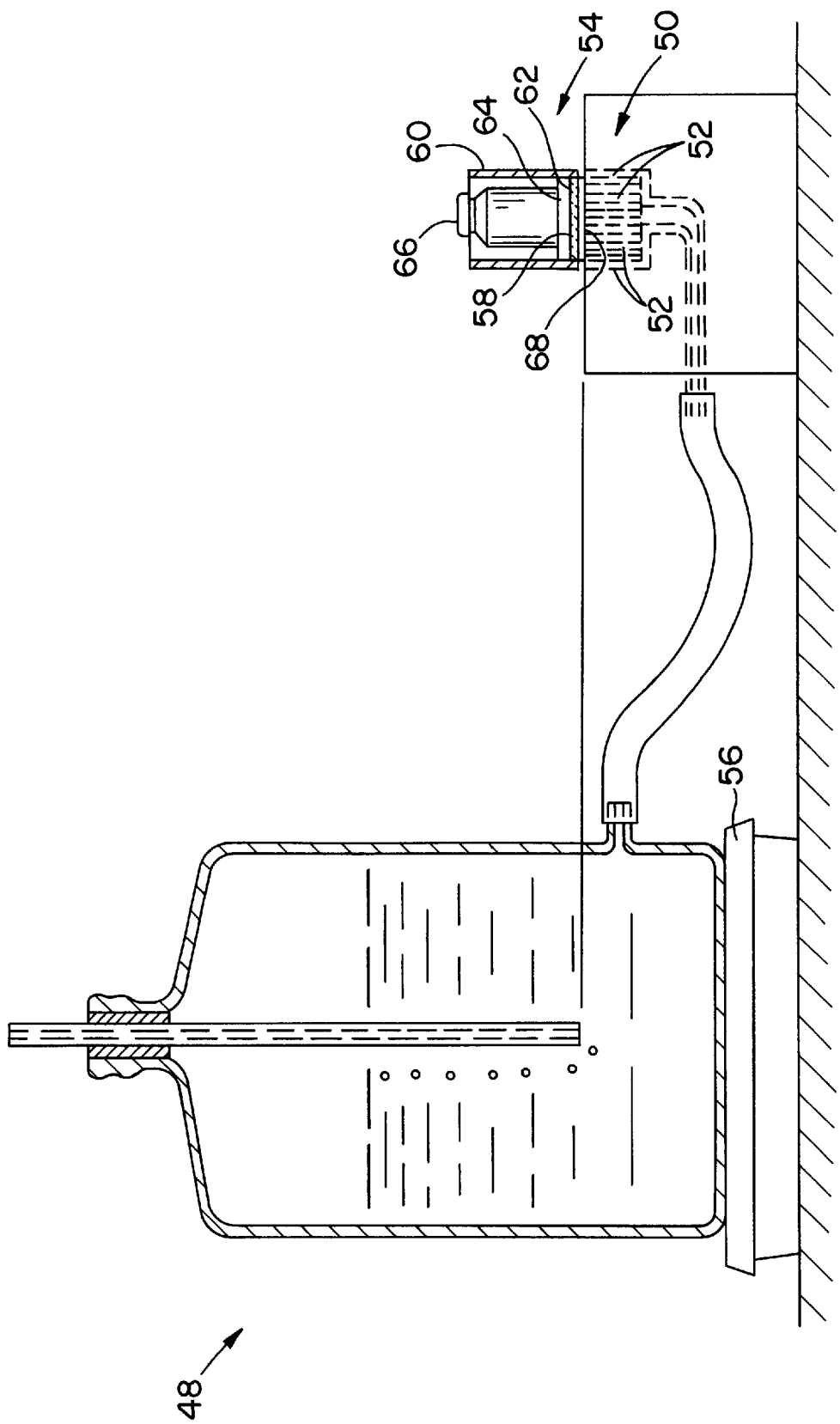
FIG. 3 is an illustration of equipment suitable for determining the Absorbency Under Load (AUL) of superabsorbent material.

The ability of a superabsorbent material to absorb a liquid while under a load is determined as follows. With reference to FIG. 3, a Demand Absorbency Tester (DAT) (48) is used, which is similar to the GATS (Gravimetric Absorbency Test System), available from M/K Systems, Danners, Mass. USA, as well as the system described by Lichstein at pages 129–142 of the INDA Technological Symposium Proceedings, March 1974. A porous plate (50) is used, having ports (52) confined within a 2.5 centimeter diameter area and covered by the Absorbency Under Load (AUL) apparatus (54). An electrobalance (56) is used to measure the flow of fluid into the superabsorbent particles (58). For this test, the fluid employed is an aqueous solution containing 0.9 weight percent sodium chloride used at room temperature.

The AUL apparatus (54) used to contain the superabsorbent particles includes a cylinder (60) made from 1 inch (2.54 centimeters) inside diameter thermoplastic tubing which is machined-out slightly to be sure of concentricity. A 100 mesh stainless steel wire cloth (62) is adhered on the bottom of cylinder (60) by means of an adhesive. Alternatively, the stainless steel wire cloth (62) can be fused to the bottom of cylinder (60) by heating the wire cloth in a flame until red hot, after which the cylinder is held onto the cloth until cooled. A soldering iron can be used to touch up the seal if unsuccessful or if it breaks. Care must be taken to maintain a flat, smooth bottom, and not distort the inside of the cylinder. A 4.4 gram piston (64) is made from 1 inch diameter solid material (e.g., Plexiglas™) and is machined to closely fit without binding in the cylinder (60). The piston (64) is used to provide the restraining load of 0.01 pound per square inch. A weight (66) is used to provide the greater degrees of restraining load. As discussed above, the greater restraining loads are 0.29 pound per square inch, 0.57 pound per square inch, and 0.90 pound per square inch. Accordingly, a 100, 200, and 317 gram weight is used to provide the respective restraining loads (in addition to the 4.4 gram piston (64) which provides the 0.01 pound per square inch loading). A sample of superabsorbent particles weighing 0.160 (±0.005) gram is utilized for testing AUL. The sample is taken from granules which are pre-screened through US standard 30 mesh and retained on US standard 50 mesh (300–600 microns), unless otherwise noted.

This test is initiated by placing a 3 centimeter diameter GF/A glass filter paper (68) onto the plate (50). The paper is sized to be larger than the internal diameter and smaller than the outside diameter of the cylinder (60) to ensure good contact while eliminating evaporation over the ports (52) of the DAT (48) and then allowing saturation to occur. The particles (58) are weighed on weighing paper and placed on the wire cloth (62) at the bottom of the AUL apparatus (54). The apparatus (54) is shaken to level the particles (58) on the wire cloth (62). Care is taken to be sure no particles are clinging to the wall of the cylinder (60). After carefully placing, without pressing, the piston (64) and, optionally, the weight (66) on the particles (58) in the cylinder (60), the AUL apparatus (54) is placed on the glass filter paper (68). The amount of fluid picked up is monitored as a function of time either directly by hand, with a strip-chart recorder, or directly into a data acquisition or personal computer system.

The amount (in grams) of fluid picked up after 60 minutes, divided by the weight of the sample (0.160 gram), is the AUL value in grams of fluid picked up per gram of sample (g/g). When the superabsorbent is a coated superabsorbent, the AUL capacity is adjusted to reflect the gram per gram capacity of the superabsorbent component as determined by the sulfated ash or other suitable procedure. The rate of fluid picked up can also be measured. Two checks can be made to ensure the accuracy of the instantaneous final readout. First, the height the piston (64) rises multiplied by the cross-sectional area of the cylinder (60) should nearly equal the amount of fluid picked up. Second, the AUL apparatus (54) can be weighed before and after the test and the difference in weight should nearly equal the fluid picked up. A minimum of three tests are performed on a given sample and averaged to assign an AUL value.

The Ball Mill Test (Absorbency Under Load Degradation Detection)

It has been observed that the Absorbency Under Load (AUL) for certain superabsorbent materials (SAMs) becomes lower when they are processed through a diaper manufacturing process. This test is designed to predict whether or not a SAM's AUL will degrade during diaper conversion.

A sample of SAM is tumbled inside a ball mill for 15 minutes. This causes abrasion to the SAM, which is similar to the amount of abrasion incurred in the diaper manufacturing process, though not by the same mechanism. After tumbling, the AUL is measured according to the method described below. The AUL of the SAM, after being converted into diapers can be estimated with the AUL value of the tumbled SAM. This test is able to predict degradation in one particular diaper process. The results may not accurately predict degradation incurred from process having different SAM/fluff ratios or debulking pressures. The SAM property most commonly affected by the diaper manufacturing process is 0.9 psi AUL. However, this test can be performed to investigate other SAM properties.

AUL, as referred to herein, is the amount of saline absorbed by 0.160 gram of SAM when the SAM is confined within a 5.07 cm$^2$ area and under a pressure of 63.4 g/cm$^2$ (0.90 psi). The term "zero head" refers to the water level in the transfer ports having slightly concave meniscus and an air bubble maintained in the tube in the aspirator bottle. When the superabsorbent is a coated superabsorbent, the AUL capacity is adjusted to reflect the gram per gram capacity of the superabsorbent component as determined by the sulfated ash or other suitable procedure.

Place approximately 127±1 gram of BURUNDUM Cylindrical Grinding Media (1991–92 Baxter Catalogue #C8775-3) into an Alumina-Fortified Grinding Jar (1994–95 Baxter Catalogue #C8750-2). Transfer 20±0.5 grams of SAM into the grinding jar. Ball mill the SAM for 15 minutes on a ball mill roller (U.S. Stoneware CV-88306 single tier jar mill) operated at approximately 150 rpm. Remove SAM from grinding jars and test for AUL described above.

Rescreen the ball milled superabsorbent material to 300–600 microns unless otherwise specified. Next, follow the 0.9 psi AUL procedure described above. This is the 0.9 AUL after Ball Milling value.

Method for Determining Retention Capacity

As used herein, the Method for Determining Retention Capacity measures the amount of test fluid that a sample of material retains after a centrifugal force has been applied. The amount of fluid retained is calculated as a gram per gram retention. The test is typically conducted under TAPPI Standard Conditions. When the test fluid is a complex fluid, such as, for example, blood, menses, artificial menses (simulant), loose passages, nasal discharges and the like, the retention capacity of a material is sometimes referred to as a complex fluid retention capacity (CFRC).

In general, testing according to this method is performed by placing a 0.5 g sample of material into a modified cylinder, exposing the sample of material to a desired fluid for 60 minutes and then placing the cylinders into a centrifuge to remove excess fluid. The results are calculated to obtain the grams of fluid retained per gram of sample of material.

Equipment and Materials

Artificial menses fluid (simulant), disclosed in U.S. Pat. No. 5,883,231, issued Mar. 16, 1999, to Achter et al. The simulant disclosed and claimed in U.S. Pat. No. 5,883,231 is commercially available from Cocalico Biologicals, Inc. 449 Stevens Rd., P.O. Box 265, Reamstown, Pa. 17567 USA.

Sorvall RT 6000D centrifuge, commercially available from Global Medical Instrumentation, Inc., 3874 Bridgewater Dr., St. Paul, Minn. 55123 USA.

Four 200 ml, screw top centrifuge bottles, commercially available from International Equipment Co., 300 Second Ave., Needham Heights, Mass. 02494 USA.

Balance, readable to 0.001 g (Note: standards should be NIST traceable and should be recertified at a frequency adequate to assure accuracy).

Four 50 ml Pyrex beakers.

Lab timer, 60 minute capacity, readable to one second, commercially available from VWR Scientific Products, 1145 Conwell Ave., Willard, Ohio 44890 USA.

Four modified Lexan cylinders, 9 cm high, 3.1 cm ID, 4.8 cm OD, with a 300 holes/in$^2$ screen attached to the bottom.

US standard 30 and 50 screen sieves, 8 inch diameter, 2 inch height, commercially available from VWR Scientific Products, 1145 Conwell Ave., Willard, Ohio 44890 USA, catalogue numbers 57334-456 and 57334-464, respectively.

Stainless steel screen, 4 holes per inch or enough open space to allow simulant to drain.

Specimen Preparation

Prepare the sample of material by using the US standard 30 and 50 screen sieves to fractionate a sample to the 300 to 600 micron size. Store the fractionated sample of material in a sealed substantially airtight container for use when the sample or samples of material will be prepared. The modified cylinder is placed on the balance and the weight tared. Place 0.5 g±0.005 g of the fractionated sample into one of the modified cylinders. Record this weight as Sample Weight. The modified cylinder containing the sample of material is weighed and this weight is recorded as Dry Cylinder Weight. Additional samples of material are placed in the three remaining modified cylinders according to the foregoing steps.

The simulant is removed from a refrigeration unit, placed on a rotator and then gently rotated for approximately 30 minutes to thoroughly mix the contents and bring the simulant to room temperature.

The steps of the testing method are as follows:

1. Approximately 10 ml of simulant are placed into a 50 ml Pyrex beaker.
2. A modified cylinder containing the sample of material is placed into the 50 ml Pyrex beaker.
3. Approximately 15 ml of simulant are poured into the modified cylinder. This ensures that the sample of material has access to the simulant from both above and below.
4. Repeat steps 1 through 3 as necessary for any desired additional sample of material.
5. After step 4 has been completed, the timer is set for 60 minutes and started.
6. After 60 minutes have elapsed, the modified cylinders are removed from the Pyrex beakers and placed on the stainless steel screen for 60 seconds.
7. After 60 seconds, the modified cylinders are removed from the stainless steel screen and placed in the 200 ml centrifuge bottles.
8. The centrifuge bottles are placed in the centrifuge for 3 minutes at 1,200 rpm.
9. After 3 minutes, the modified cylinders are removed from the centrifuge bottles and the modified cylinders containing the samples of material are weighed. This weight is recorded as Wet Cylinder Weight.

The Retention Capacity of each sample of absorbent is then calculated according to the following formula:

$$\frac{[(\text{Wet Cylinder Weight} - \text{Dry Cylinder Weight}) - \text{Product Weight}]}{(\text{Product Weight})}$$

Where reported in any of the following examples, the Retention Capacities are an average of two samples (i.e., n=2).

Centrifuge Retention Capacity Test Method

As used herein, the Centrifugal Retention Capacity (CRC) is a measure of the absorbent capacity of the superabsorbent material retained after being subjected to centrifugation under controlled conditions. The CRC can be measured by placing 0.200±0.005 grams of the sample material (coated or uncoated superabsorbent) to be tested into a water-permeable bag which will contain the sample while allowing the test solution (0.9 percent NaCl solution) to be freely absorbed by the sample. A heat-sealable tea bag material (available from Dexter Nonwovens of Windsor Locks, Conn., U.S.A., as item #11697) works well for most applications. The bag is formed by folding a 5-inch by 3-inch sample of the bag material in half and heat sealing two of the open edges to form a 2.5-inch by 3-inch rectangular pouch. The heat seals should be about 0.25 inch inside the edge of the material. After the sample is placed in the pouch, the remaining open edge of the pouch is also heat-sealed. Empty bags are also made to be tested with the sample bags as controls. Three sample bags are tested for each superabsorbent material.

The sealed bags are placed between two Teflon®-coated fiberglass screens having 0.25-inch openings (Taconic Plastics, Inc., Petersburg, N.Y.) and submerged in a pan of 0.9 percent NaCl solution at 73.4°±2° Fahrenheit, making sure that the screens are held down until the bags are completely wetted. After wetting, the samples remain in the solution for 30 minutes, at which time they are removed from the solution and temporarily laid on a non-absorbent flat surface. The wet bags are then placed into the basket of a suitable centrifuge capable of subjecting the samples to a g-force of 350. (A suitable centrifuge is a Heraeus LABOFUGE 400, Heraeus Instruments part number 75008157, available from Heraeus infosystems GmbH, Hanau, Germany). The samples must be placed in opposing positions within the centrifuge to balance the basket when spinning. The bags are centrifuged at a target of 1600 rpm, but within the range of 1500–1900 rpm, for 3 minutes (target g-force of 350). The bags are removed and weighed, with the empty bags (controls) being weighed first, followed by the bags containing superabsorbent material. The amount of fluid absorbed and retained by the superabsorbent material, taking into account the fluid retained by the bag material alone, is the Centrifugal Retention Capacity of the superabsorbent material, expressed as grams of fluid per gram of superabsorbent material. When the superabsorbent is a coated superabsorbent, the retention capacity is adjusted to reflect the gram per gram capacity of the superabsorbent component as determined by the sulfated ash procedure or other suitable method.

EXAMPLES

The following Examples serve to illustrate the effect that different coating materials have on the AUL values of the superabsorbent-containing composites of the present invention. The superabsorbent material utilized in this Example was either DRYTECH® 2035, a polyacrylate superabsorbent material commercially available from Dow Chemical Company, Midland, Mich. USA, or FAVOR SXM 880, a polyacrylate superabsorbent material commercially available from Stockhausen, Inc. Greensboro, N.C. USA. Typical 0.9 psi AUL values for uncoated FAVOR SXM 880 are in a range of 22 to 23 grams/gram, and after ball milling are typically 12 to 18 grams/gram. Typical 0.9 psi AUL values for uncoated DRYTECH 2035 are in a range of 14 to 16 grams/gram, and after ball milling are typically 10 to 12 grams/gram. These AUL values are for a 300 to 600 micron particle size distribution.

The coating material of these Examples was either EXCEL 110, a cellulose powder commercially available from Functional Foods, Elizabethtown, N.J., U.S.A., SULFATATE HJ, a hardwood pulp available from Rayonier, Inc., Jesup, Ga., U.S.A., ZEOFREE 5175A, a granulated, precipitated silica commercially available from J. M. Huber, Havre de Grace, Md., U.S.A., combinations of EXCEL 110 and ZEOFREE 5175A, SILKLEER 25M, a fine particle, mined, processed perlite available from Silbrico Corporation, Hodgkins, Ill., or RYOLEX 39, a coarser, mined processed perlite available from Silbrico Corporation, Hodgkins, Ill. The superabsorbent-containing composites of this Example were prepared at The Coating Place, Verona, Wis., U.S.A., using a process described herein. The association agent utilized was distilled water. The superabsorbent material, the coating material(s) and the association agent were added in the amounts indicated in Tables 1, 3, 5, 7, and 9. The process provided for the addition of the coating material(s) to a fluidized bed coating apparatus. While the coating material(s) was (were) being fluidized, the association agent was added to the process. After the association agent was added, the superabsorbent material was added to the process. In some cases the temperature was raised in the fluidized bed coating process until the air outlet temperature equaled approximately 44° C., when the run was considered complete. This effectively dried the coated superabsorbent. Alternatively, the fluidizing was continued at an outlet temperature approximating that of the inlet temperature (i.e., room temperature). This alternative process is a more economical process for producing this type of material as additional energy is not needed. Which process was used is indicated in Tables 1 and 3. Materials described in Tables 5–10 were heated. Coated materials in Tables 1–10 used a 300 to 850 micron particle size range for AUL and after Ball Mill AUL testing.

TABLE 1

Samples of FAVOR SXM 880 Coated With EXCEL 110

| Sample | Heated to 44° C. | SAM: Coating (ratio x:1) | SAM: Water (ratio x:1) | Coating: Water (ratio x:1) | SAM (%) |
|---|---|---|---|---|---|
| 1a | No | 2.0 | 2.0 | 1.0 | 73.8 |
| 2a | No | 2.0 | 4.0 | 2.0 | 74.4 |
| 3a | No | 2.0 | 8.0 | 4.0 | 77.9 |
| 4a | Yes | 2.0 | 2.0 | 1.0 | 74.2 |
| 5a | Yes | 1.0 | 1.0 | 1.0 | 81.7 |
| 6a | Yes | 3.0 | 3.0 | 1.0 | 84.0 |

TABLE 2

AUL Values of Samples in Table 1 (FAVOR SXM 880 Coated With EXCEL 110) in Comparison to Uncoated FAVOR SXM 880

| Sample | 0.9 AUL | 0.9 AUL after Ball Mill | 0.9 AUL uncoated SAM | 0.9 AUL uncoated SAM after Ball Mill |
|---|---|---|---|---|
| 1a | 22.07 | 22.10 | 22–23 | 12–18 |
| 2a | 22.31 | 21.98 | 22–23 | 12–18 |
| 3a | 23.06 | 23.50 | 22–23 | 12–18 |
| 4a | 21.95 | 22.94 | 22–23 | 12–18 |
| 5a | 23.97 | 23.89 | 22–23 | 12–18 |
| 6a | 22.92 | 22.48 | 22–23 | 12–18 |

TABLE 3

Samples of DRYTECH 2035 Coated With EXCEL 110

| Sample | Heated to 44° C. | SAM: Coating (ratio x:1) | SAM: Water (ratio x:1) | Coating: Water (ratio x:1) | SAM (%) |
|---|---|---|---|---|---|
| 1b | No | 2.0 | 2.0 | 1.0 | 64.29 |
| 2b | No | 2.0 | 4.0 | 2.0 | 58.88 |
| 3b | No | 2.0 | 8.0 | 4.0 | 75.43 |
| 4b | Yes | 2.0 | 2.0 | 1.0 | 59.36 |
| 5b | Yes | 1.0 | 1.0 | 1.0 | 40.44 |
| 6b | Yes | 3.0 | 2.7 | 0.9 | 71.36 |

TABLE 4

AUL Values of Samples in Table 3 (DRYTECH 2035 Coated With EXCEL 110) in Comparison to Uncoated DRYTECH 2035

| Sample | 0.9 AUL | 0.9 AUL after Ball Mill | 0.9 AUL uncoated SAM | 0.9 AUL uncoated SAM after Ball Mill |
|---|---|---|---|---|
| 1b | 22.29 | 22.40 | 14–16 | 10–12 |
| 2b | 24.37 | 22.44 | 14–16 | 10–12 |
| 3b | 21.77 | 21.08 | 14–16 | 10–12 |
| 4b | 22.88 | 24.33 | 14–16 | 10–12 |
| 5b | 27.20 | 25.96 | 14–16 | 10–12 |
| 6b | 21.86 | 21.16 | 14–16 | 10–12 |

TABLE 5

Samples of Various Superabsorbents Coated With Various Adsorbent Coatings

| Sample | SAM | Coating | SAM: Coating (ratio x:1) | SAM: Water (ratio x:1) | Coating: Water (ratio x:1) | SAM (%) |
|---|---|---|---|---|---|---|
| 1c | Favor | Zeofree | 2 | 2.0 | 1.00 | 80.5 |
| 2c | Favor | Zeofree | 4 | 2.0 | 0.50 | 84.8 |
| 3c | Drytech | Zeofree | 2 | 2.0 | 1.00 | 78 |
| 4c | Drytech | Zeofree | 4 | 2.0 | 0.50 | 89 |
| 5c | Favor | Silkleer | 12.82 | 6.0 | 0.47 | 96.1 |
| 6c | Favor | Ryolex | 8.57 | 6.0 | 0.70 | 95.2 |

TABLE 6

AUL Values of Samples in Table 5 in Comparison to Uncoated Superabsorbents

| Sample | 0.9 AUL | 0.9 AUL after Ball Mill | 0.9 AUL uncoated SAM | 0.9 AUL uncoated SAM after Ball Mill |
|---|---|---|---|---|
| 1c | 20.66 | 17.11 | 22–23 | 12–18 |
| 2c | 19.02 | 16.10 | 22–23 | 12–18 |
| 3c | 18.94 | 18.78 | 14–16 | 10–12 |
| 4c | 17.20 | 15.49 | 14–16 | 10–12 |
| 5c | 20.47 | 16.19 | 22–23 | 12–18 |
| 6c | 19.43 | 17.25 | 22–23 | 12–18 |

TABLE 7

Samples of FAVOR SXM 880 Coated With EXCEL 110 and ZEOFREE

| Sample | SAM: Zeofree (x:1) | SAM: Excel (x:1) | Excel: Zeofree (x:1) | SAM: Water (x:1) | SAM (%) | Excel (%) | Zeofree (%) |
|---|---|---|---|---|---|---|---|
| 1d | 10 | 2 | 5 | 1.67 | 69.04 | 25.46 | 5.51 |
| 2d | 10 | 2 | 5 | 1.67 | 78.4 | 20.7 | 0.9 |
| 3d | 3.33 | 3.33 | 1 | 1.67 | 80.9 | 11.5 | 7.7 |
| 4d | 3 | 6 | 0.5 | 2.00 | 81.8 | 7.6 | 10.6 |
| 5d | 2 | 10 | 0.2 | 1.67 | 75.7 | 10.8 | 13.5 |

TABLE 7-continued

Samples of FAVOR SXM 880 Coated With EXCEL 110 and ZEOFREE

| Sample | SAM:<br>Zeofree<br>(x:1) | SAM:<br>Excel<br>(x:1) | Excel:<br>Zeofree<br>(x:1) | SAM:<br>Water<br>(x:1) | SAM<br>(%) | Excel<br>(%) | Zeofree<br>(%) |
|---|---|---|---|---|---|---|---|
| 6d | 2 | 20 | 0.1 | 1.82 | 82.9 | 6.5 | 10.6 |
| 7d | 5 | 1 | 5 | 0.83 | 73 | 25.9 | 1.1 |

TABLE 8

AUL Values of Samples in Table 7 (FAVOR SXM 880 Coated With EXCEL 110 and ZEOFREE) in Comparison to Uncoated FAVOR SXM 880

| Sample | 0.9 AUL | 0.9 AUL after Ball Mill | 0.9 AUL uncoated SAM | 0.9 AUL uncoated SAM after Ball Mill |
|---|---|---|---|---|
| 1d | 23.96 | 21.58 | 22–23 | 12–18 |
| 2d | 21.26 | 21.15 | 22–23 | 12–18 |
| 3d | 21.17 | 18.80 | 22–23 | 12–18 |
| 4d | 19.35 | 18.59 | 22–23 | 12–18 |
| 5d | 21.60 | 19.76 | 22–23 | 12–18 |
| 6d | 19.63 | 17.26 | 22–23 | 12–18 |
| 7d | 21.95 | 21.29 | 22–23 | 12–18 |

TABLE 9

Samples of DRYTECH 2035 Coated With EXCEL 110 and ZEOFREE

| Sample | SAM:<br>Zeofree<br>(x:1) | SAM:<br>Excel<br>(x:1) | Excel:<br>Zeofree<br>(x:1) | SAM:<br>Water<br>(x:1) | SAM<br>(%) | Excel<br>(%) | Zeofree<br>(%) |
|---|---|---|---|---|---|---|---|
| 1e | 10 | 2 | 5 | 3.33 | 57.44 | 41.47 | 1.09 |
| 2e | 10 | 2 | 5 | 1.67 | 60.85 | 36.54 | 2.62 |
| 3e | 3.33 | 3.33 | 1 | 1.67 | 75.47 | 19.59 | 4.94 |
| 4e | 3 | 6 | 0.5 | 2.00 | 81.8 | 6.7 | 11.5 |
| 5e | 2 | 10 | 0.2 | 1.67 | 74.6 | 12.01 | 13.38 |
| 6e | 2 | 20 | 0.1 | 1.82 | 68.2 | 12.9 | 18.9 |

TABLE 10

AUL Values of Samples in Table 9 (DRYTECH 2035 Coated With EXCEL 110 and ZEOFREE) in Comparison to Uncoated DRYTECH

| Sample | 0.9 AUL | 0.9 AUL after Ball Mill | 0.9 AUL uncoated SAM | 0.9 AUL uncoated SAM after Ball Mill |
|---|---|---|---|---|
| 1e | 23.90 | 23.07 | 14–16 | 10–12 |
| 2e | 22.43 | 21.74 | 14–16 | 10–12 |
| 3e | 20.15 | 18.80 | 14–16 | 10–12 |
| 4e | 18.06 | 18.46 | 14–16 | 10–12 |
| 5e | 19.57 | 20.42 | 14–16 | 10–12 |
| 6e | 22.39 | 22.21 | 14–16 | 10–12 |

As can be seen in Tables 3–6, 9 and 10, the coating on DRYTECH 2035 enhances AUL over the uncoated superabsorbent both before and after ball milling. As can be seen in Tables 1, 2, and 5–8, the coating on FAVOR SXM 880 maintains AUL after ball milling. Mixed coatings provide a protection benefit, as can be seen in Tables 7–10, but may also provide other benefits such as control of gel bed permeability to create either a high wicking or a rapid intake structure, controlled rate of fluid absorption, and others.

Alternatively to the EXCEL 110 cellulose coating, a coating of conventional cellulose pulp fibers typically used in personal care products can be used. Current absorbent cores of diapers consist of superabsorbents and fibers. These two elements are mixed together but are not bonded. Coating of the pulp fibers onto the superabsorbent particles are one way to increase integrity, achieve less shakeout and reduce the amount of pulp fiber needed in the absorbent composite, leading to thinner structures. The following example describes such a material with superabsorbent coated with SULFATATE HJ, a mercerized hardwood pulp fiber, available from Rayonier Inc., Jesup, Ga., U.S.A.

In a separate mixer, superabsorbent and water are mixed to swell the superabsorbent in a pre-designed ratio. The pulp is placed into the reaction vessel and distilled water added. The preswelled superabsorbent is then added to the reaction vessel. After approximately ten minutes of mixing, the air temperature is increased until the air outlet temperature reaches 130° Fahrenheit. The coated superabsorbent was not prescreened to a particular particle size, but was tested as is.

TABLE 11

AUL Values of FAVOR SXM 880 Coated with SULFATATE HJ Pulp

| Sample | SAM | SAM:<br>Coating<br>(ratio x:1) | SAM:<br>Water<br>(ratio x:1) | Coating:<br>Water<br>(ratio x:1) | SAM<br>(%) |
|---|---|---|---|---|---|
| 1f | Favor | 9 | 0.5 | 0.5 | 95.1 |

TABLE 12

AUL Values of Sample in Table 11 in Comparison to Uncoated FAVOR SXM 880

| Sample | 0.9 AUL | 0.9 AUL after Ball Mill | 0.9 AUL uncoated SAM | 0.9 AUL uncoated SAM after Ball Mill |
|---|---|---|---|---|
| 1f | 19.2 | 19.0 | 22–23 | 12–18 |

As can be seen in Table 12, the coating on FAVOR SXM 880 is somewhat effective after ball milling. Coating of DRYTECH 2035 with SULFATATE HJ under the same conditions produced a coated superabsorbent with an 84.9 percent superabsorbent component. Thus the DRYTECH 2035 coated superabsorbent had a higher level of coating than the FAVOR SXM 880 coated superabsorbent, similar to examples in Table 3. A similar protective benefit and increased AUL would be expected with the DRYTECH 2035 coated with SULFATATE HJ, especially with the higher level of coating.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. An inhomogeneously crosslinked superabsorbent particle comprising:
   a particulate coating covering the superabsorbent particle, the coated superabsorbent particle having an absorbency under load value at 0.9 psi, wherein at least 50% of the absorbency under load value at 0.9 psi is maintained subsequent to the coated superabsorbent particle undergoing a ball mill test.

2. The superabsorbent particle of claim 1, wherein at least 75% of the absorbency under load value at 0.9 psi is maintained subsequent to the coated superabsorbent particle undergoing a ball mill test.

3. The superabsorbent particle of claim 1, wherein at least 90% of the absorbency under load value at 0.9 psi is maintained subsequent to the coated superabsorbent particle undergoing a ball mill test.

4. The superabsorbent particle of claim 1, wherein the absorbency under load value at 0.9 psi of the coated superabsorbent particle is greater than an absorbency under load value at 0.9 psi of the superabsorbent particle without the coating.

5. The superabsorbent particle of claim 1, wherein the absorbency under load value at 0.9 psi of the coated superabsorbent particle is greater than an absorbency under load value at 0.9 psi of the superabsorbent particle without the coating subsequent to the uncoated superabsorbent particle undergoing a ball mill test.

6. The superabsorbent particle of claim 1, wherein the coated superabsorbent particle has an absorbency under load value at 0.9 psi of at least 7 grams/gram.

7. The superabsorbent particle of claim 1, wherein the coated superabsorbent particle has an absorbency under load value at 0.9 psi of at least 9 grams/grain.

8. The superabsorbent particle of claim 1, wherein the coated superabsorbent particle has an absorbency under load value at 0.9 psi of at least 15 grams/gram.

9. The superabsorbent particle of claim 1, wherein the coated superabsorbent particle has an absorbency under load value at 0.9 psi of at least 20 grams/gram.

10. The superabsorbent particle of claim 1, wherein the coated superabsorbent particle has an absorbency under load value at 0.9 psi of at least 24 grams/gram.

11. The superabsorbent particle of claim 1, wherein the coated superabsorbent particle has an absorbency under load value at 0.9 psi of at least 27 grams/grain.

12. The superabsorbent particle of claim 1, wherein the superabsorbent particle is coated with a fibrous coating.

13. The superabsorbent particle of claim 1, wherein the superabsorbent particle is coated with a nonfibrous coating.

14. The superabsorbent particle of claim 1, wherein the superabsorbent particle is coated with a resilient coating.

15. The superabsorbent particle of claim 1, wherein the superabsorbent particle is covered with multiple coatings.

16. The superabsorbent particle of claim 1, wherein the coating extends over at least about 20% of a surface of the superabsorbent particle.

17. The superabsorbent particle of claim 1, wherein the coating extends over at least about 50% of a surface of the superabsorbent particle.

18. The superabsorbent particle of claim 1, wherein the coating extends over at least about 70% of a surface of the superabsorbent particle.

19. The superabsorbent particle of claim 1, wherein the coating extends over at least about 90% of a surface of the superabsorbent particle.

20. An absorbent composite comprising:
    an inhomogeneously crosslinked superabsorbent polymer including a plurality of fibers attached to an outer surface of the polymer, wherein a number of the plurality of fibers extends from the outer surface at an angle substantially perpendicular to the outer surface.

21. The absorbent composite of claim 20, wherein the inhomogeneous crosslinked superabsorbent polymer is in the form of a shell-core composition.

22. The absorbent composite of claim 20, wherein the superabsorbent polymer has an absorbency under load value at 0.9 psi of at least 7 grams/gram.

23. The absorbent composite of claim 20, wherein the superabsorbent polymer has an absorbency under load value at 0.9 psi of at least 9 grams/gram.

24. The absorbent composite of claim 20, wherein the superabsorbent polymer has an absorbency under load value at 0.9 psi of at least 15 grams/gram.

25. The absorbent composite of claim 20, wherein the superabsorbent polymer has an absorbency under load value at 0.9 psi of at least 20 grams/gram.

26. The absorbent composite of claim 20, wherein the superabsorbent polymer has an absorbency under load value at 0.9 psi of at least 24 grams/gram.

27. The absorbent composite of claim 20, wherein the superabsorbent polymer has an absorbency under load value at 0.9 psi of at least 27 grams/gram.

28. The absorbent composite of claim 20, wherein the absorbent composite has an absorbency under load value at 0.9 psi that is maintained or increases as a result of being subjected to a ball mill test, compared to an absorbency under load value at 0.9 psi of the absorbent composite prior to the ball mill test.

29. The absorbent composite of claim 20, wherein the absorbent composite has an absorbency under load value at 0.9 psi greater than an absorbency under load value at 0.9 psi of uncoated superabsorbent material.

30. The absorbent composite of claim 20, wherein the plurality of fibers comprise a material selected from the group consisting of natural cellulosic materials and synthetic cellulosic materials.

31. The absorbent composite of claim 20, wherein the plurality of fibers comprise a material selected from the group consisting of wood pulp, powdered cellulose, non-woody cellulose materials, regenerated cellulose, cellulose derivatives, and combinations thereof.

32. The absorbent composite of claim 20, comprising between 30% and 97% of the superabsorbent polymer.

33. The absorbent composite of claim 20, comprising between 40% and 95% of the superabsorbent polymer.

34. The absorbent composite of claim 20, comprising between 50% and 92% of the superabsorbent polymer.

35. The absorbent composite of claim 20, comprising between 60% and 90% of the superabsorbent polymer.

36. The absorbent composite of claim 20, wherein the absorbent composite has a complex fluid retention capacity of between 0 and about 30 grams/gram.

37. The absorbent composite of claim 20, wherein the absorbent composite has a complex fluid retention capacity of between about 5 and about 30 grams/gram.

38. The absorbent composite of claim 20, wherein the absorbent composite has a complex fluid retention capacity of between about 10 and about 30 grams/gram.

39. The absorbent composite of claim 20, wherein the absorbent composite has a complex fluid retention capacity of between about 12 and about 30 grams/gram.

40. The absorbent composite of claim 20, wherein the absorbent composite has a complex fluid retention capacity of between about 13 and about 30 grains/gram.

41. The absorbent composite of claim 20, wherein the absorbent composite has a complex fluid retention capacity of between about 15 and about 30 grams/gram.

42. The absorbent composite of claim 20, wherein the absorbent composite has a complex fluid retention capacity of between about 18 and about 30 grams/gram.

43. The absorbent composite of claim 20, wherein each of the plurality of fibers comprises a first end attached to the outer surface and a second end unattached to the outer surface.

44. The absorbent composite of claim 20, wherein the absorbent composite comprises multiple coating materials.

45. An absorbent article comprising the absorbent composite of claim 20.

46. An absorbent composite comprising:
an inhomogeneously crosslinked superabsorbent polymer in a shell-core form having a highly crosslinked outer shell, including a plurality of fibers attached to the outer shell and each of the plurality of fibers extends from the outer shell at an angle substantially perpendicular to the outer shell.

47. An absorbent composite comprising:
an inhomogeneously crosslinked superabsorbent polymer;
a protective, fibrous coating material; and
an association agent, wherein fibers within the fibrous coating are attached to an outer surface of the polymer by at least one end and extend outward away from the outer surface of the polymer.

48. The absorbent composite of claim 47, wherein the inhomogeneous crosslinked superabsorbent polymer is in the form of a shell-core composition.

49. The absorbent composite of claim 47, wherein the absorbent composite has an absorbency under load value at 0.9 psi that is maintained or increases as a result of being subjected to a ball mill test, compared to an absorbency under load value at 0.9 psi of the absorbent composite prior to the ball mill test.

50. The absorbent composite of claim 47, wherein the absorbent composite has an absorbency under load value at 0.9 psi of at least 9 grams/gram.

51. The absorbent composite of claim 47, wherein the absorbent composite has an absorbency under load value at 0.9 psi of at least 15 grams/gram.

52. The absorbent composite of claim 47, wherein the absorbent composite has an absorbency under load value at 0.9 psi of at least 20 grams/gram.

53. The absorbent composite of claim 47, comprising between 30% and 97% of the superabsorbent polymer.

54. The absorbent composite of claim 47, comprising between 40% and 95% of the superabsorbent polymer.

55. The absorbent composite of claim 47, comprising between 50% and 92% of the superabsorbent polymer.

56. The absorbent composite of claim 47, comprising between 60% and 90% of the superabsorbent polymer.

57. The absorbent composite of claim 47, wherein the association agent is applied to at least one of the superabsorbent polymer and the protective, fibrous coating material in an amount of from about 2 parts of association agent to 1 part of coating to about 0.1 part of association agent to 1 part of coating.

58. The absorbent composite of claim 47, wherein the superabsorbent polymer and the protective, fibrous coating material are present in the absorbent composite in a weight ratio of about 30:70 to about 97:3.

59. The absorbent composite of claim 47, wherein the superabsorbent polymer and the protective, fibrous coating material are present in the absorbent composite in a weight ratio of about 40:60 to about 80:20.

60. The absorbent composite of claim 47, wherein the superabsorbent polymer and the protective, fibrous coating material are present in the absorbent composite in a weight ratio of about 60:40 to about 70:30.

61. The absorbent composite of claim 47, wherein the protective, fibrous coating material comprises an absorbent material.

62. The absorbent composite of claim 47, wherein the protective, fibrous coating material comprises an adsorbent material.

63. The absorbent composite of claim 47, wherein the protective, fibrous coating material comprises a hydrophilic material.

64. The absorbent composite of claim 63, wherein the hydrophilic material is selected from the group consisting of natural cellulosic materials and synthetic cellulosic materials.

65. The absorbent composite of claim 63, wherein the hydrophilic material is selected from the group consisting of wood pulp, powdered cellulose, non-woody cellulose materials, regenerated cellulose, cellulose derivatives, and combinations thereof.

66. The absorbent composite of claim 47, wherein the protective, fibrous coating material comprises microcrystalline cellulose powder.

67. The absorbent composite of claim 47, wherein the association agent is selected from the group consisting of water, volatile organic solvents, aqueous solutions of film-forming materials, synthetic adhesives, and combinations thereof.

68. The absorbent composite of claim 47, wherein the coating material comprises multiple coating materials.

69. An absorbent article comprising the absorbent composite of claim 47.

70. An absorbent composite comprising:
an inhomogeneously crosslinked superabsorbent polymer having a highly crosslinked outer shell; and
a particulate protective coating material covering the outer shell of the superabsorbent polymer.

71. The absorbent composite of claim 70, wherein the protective coating material extends over at least about 20% of the outer shell of the superabsorbent polymer.

72. The absorbent composite of claim 70, wherein the protective coating material extends over at least about 50% of the outer shell of the superabsorbent polymer.

73. The absorbent composite of claim 70, wherein the protective coating material extends over at least about 70% of the outer shell of the superabsorbent polymer.

74. The absorbent composite of claim 70, wherein the protective coating material extends over at least about 90% of the outer shell of the superabsorbent polymer.

75. The absorbent composite of claim 70, wherein the absorbent composite has an absorbency under load value at 0.9 psi that is maintained or increases as a result of being subjected to a ball mill test, compared to an absorbency under load value at 0.9 psi of the absorbent composite prior to the ball mill test.

76. The absorbent composite of claim 70, wherein the absorbent composite has an absorbency under load value at 0.9 psi of at least 9 grams/gram.

77. The absorbent composite of claim 70, wherein the absorbent composite has an absorbency under load value at 0.9 psi of at least 15 grams/gram.

78. The absorbent composite of claim 70, wherein the absorbent composite has an absorbency under load value at 0.9 psi of at least 20 grams/gram.

79. The absorbent composite of claim 70, comprising between 30% and 97% of the superabsorbent polymer.

80. The absorbent composite of claim 70, comprising between 40% and 95% of the superabsorbent polymer.

81. The absorbent composite of claim 70, comprising between 50% and 92% of the superabsorbent polymer.

82. The absorbent composite of claim 70, comprising between 60% and 90% of the superabsorbent polymer.

83. The absorbent composite of claim 70, wherein the protective coating material comprises an absorbent material.

84. The absorbent composite of claim 70, wherein the protective coating material comprises an adsorbent material.

85. The absorbent composite of claim 70, wherein the protective coating material comprises a hydrophilic material.

86. The absorbent composite of claim 85, wherein the hydrophilic material is selected from the group consisting of natural cellulosic materials and synthetic cellulosic materials.

87. The absorbent composite of claim 85, wherein the hydrophilic material is selected from the group consisting of wood pulp, powdered cellulose, non-woody cellulose materials, regenerated cellulose, cellulose derivatives, and combinations thereof.

88. The absorbent composite of claim 70, wherein the protective coating material comprises a fibrous material.

89. The absorbent composite of claim 70, wherein the protective, fibrous coating material comprises microcrystalline cellulose powder.

90. The absorbent composite of claim 70, wherein the coating material comprises multiple coating materials.

91. An absorbent article comprising the absorbent composite of claim 70.

* * * * *